CHRYSANTHEMUM PLANT
Filed Feb. 2, 1973
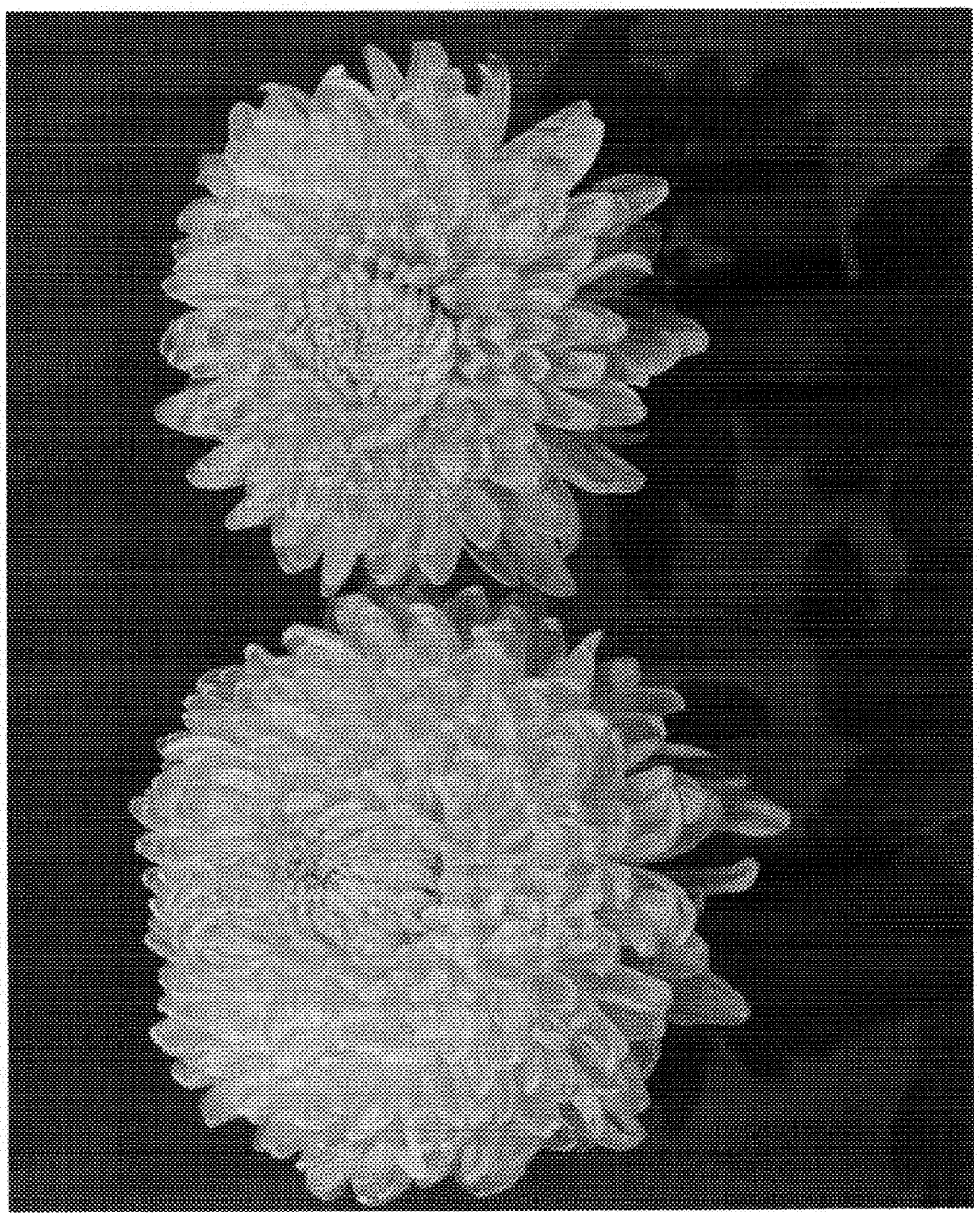

United States Patent Office

Plant Pat. 3,594
Patented Aug. 20, 1974

3,594

CHRYSANTHEMUM PLANT

Walter H. Jessel, Jr., Doylestown, and William E. Duffett, Akron, Ohio, assignors to Yoder Brothers, Inc., Barberton, Ohio

Filed Feb. 2, 1973, Ser. No. 329,048
Int. Cl. A01h *5/00*
U.S. Cl. Plt.—78 1 Claim

The present invention comprises a new and distinct cultivar of incurved, standard form chrysanthemum plant known by the varietal name Southern Belle, which is a sport of an unpatented cultivar known in the United States as Southern Comfort.

The new cultivar is similar in many respects to the cultivar Southern Gold, the subject matter of U.S. Plant Pat. No. 3,257. The new cultivar has the same characteristics as Southern Gold of:

1. Intense yellow color on petal face and center of flower.
2. Sharp and reliable response at temperatures above 70°.
3. Foliage shape, color and form.
4. Vigor, response and habit of growth.
5. Recommended flowering period of value.

The new cultivar is distinguished from Southern Gold by the following characteristics when grown under comparable conditions:

1. Approximately a ½" to ¾" larger flower size which results in a slightly higher percentage of cut in the top two grades (SAF Standards), fewer culls, and less variation in flower size within a plot.
2. A more incurved flower form with no swirl in center of flower as observed in Southern Gold.
3. Improved form retention which provides approximately 2 to 4 days increased bench life and home life.

4. A less intense yellow color on the reverse side of the petals.

The new cultivar was selected from a flowering block of the parent cultivar in Barberton, Ohio, and when asexually reproduced by cuttings at Barberton, Ohio, has been found to retain its distinctive characteristics through succeive propagation.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from June through October, and in the southern United States, from April through mid-November.

The accompanying photographic drawing shows the unique characteristics of the new cultivar, with the color being as nearly true as possible with color illustrations of this type. The photograph vividly displays the characteristics of the new cultivar as compared with Southern Gold, with the new cultivar appearing on the left and Southern Gold on the right.

The yellow flower color of both the new and parent cultivar is slightly darker in the photograph than in actual appearance, with the true colors being set forth in the color references below.

In the description which follows, color references are made to the Munsell Color Book, 1963 edition, and comparisons are made with the cultivar Southern Gold. Where only a value or description appears only for the new cultivar, the same value or description applies as well to Southern Gold. The grade data presented also includes the parent cultivar Southern Sun.

Botanical classification: *Chrysanthemum morifolium*

| | Southern Belle | Southern Gold |
|---|---|---|
| Bloom: | | |
| Size | 6" to 6½" | 5½" to 6". |

Grade data: Averaged Percentages for a Summer's Flowering Performance in 1972 at Barberton, Ohio (based on Society of American Florist Grade Data)

| | Blue | Red | Green | Culls |
|---|---|---|---|---|
| Southern Belle | 40 | 48 | 5 | 7 |
| Southern Gold | 34 | 47 | 9 | 10 |
| Southern Sun | 31 | 46 | 11 | 12 |

| | Southern Belle | Southern Gold |
|---|---|---|
| Bloom (contd.): | | |
| Fully expanded | 6¾" to 7¼" | 6" to 6¾". |
| Borne | Singly on disbudded plants | |
| Stems | Strong | |
| Form | Semi-incurved | Moderately incurved. |
| Permanence | 12–14 days | 8–12 days. |
| Color (Munsell): | | |
| Center of flower | Golden yellow, 7.5Y8.5/10 | |
| Base of petals | do | |
| Inside of petals | do | |
| Reverse of petals | Yellow, 7.5Y9/4 | Golden yellow, 7.5Y8.5/6. |
| Tonality from a distance | Golden yellow | |
| Discloration | Golden yellow, 7.5Y8.5/10 | |
| Petals: | | |
| Texture | Smooth | |
| Appearance and form | Sharply keeled at base, narrow with a blunt point | |
| Arrangement | Composite, whorled on a single receptacle | |
| Persistence | Resists shatter | |
| Fragrance | Typical chrysanthemum | |
| Reproductive organs: | | |
| Stamen, anthers | None | |
| Pollen | do | |
| Arrangement | Clustered in center of flower, if present | |
| Styles | Present ray florets | |
| Length | Short | |
| Ovaries | At the base of petal attached to receptacle | |
| Plant: | | |
| Form | Herbaceous | |
| Growth | Upright | |
| Height | Approximately 46"–54" given 2 long day weeks and 11 week total crop time as defined in the timetables of Yoder Brothers, Inc., Barberton, Ohio, for the various seasons of the year. | |
| Spread | None grown single stem to slight when pinched | |

TABLE—Continued

| | Southern Belle | Southern Gold |
|---|---|---|
| Foliage: | | |
| Top side | Dark green, 7.5GY2/4 | |
| Size | 11:7 length to width ratio, up to 5½" long, and 3½" wide | |
| Quantity | Numerous | |
| Shape | Spatulate lobed | |
| Texture | Coarse | |
| Ribs and veins | Prominent | |
| Edge | Indented | |
| Serration | Moderate | |
| Under side | Light green, 7.5GY4/4 | |
| Stipules | Present | |

We claim:

1. A new and distinct cultivar of chrysanthemum characterized particularly as to uniqueness when compared to the cultivar Southern Gold by its approximately ½" to ¾" larger flower size which results in a slightly higher percentage of cut in the top two grades (SAF Standards), with few culls and less variation in flower size within a plot; by its more incurved flower form with no swirl in the center of the flower as observed in Southern Gold, and by its improved form retention which provides approximately 2 to 4 days increased bench life and homelife.

No references cited.

ROBERT E. BAGWILL, Primary Examiner

UNITED STATES PATENT OFFICE

CERTIFICATE OF CORRECTION

PATENT NO. PP-3594

DATED August 20, 1974

INVENTOR(S) WALTER H. JESSEL, JR. and WILLIAM E. DUFFETT

It is certified that error appears in the above-identified patent and that said Letters Patent are hereby corrected as shown below:

Column 2, line 7, change "ceive propagation" to --cessive propagations--.

Column 2, line 26, chould be part of the previous paragraph.

Column 2, line 36, "Southern Sun" should be --Southern Comfort--.

In the tabulation, under Grade Data:, "Southern Sun" should be --Southern Comfort--.

Signed and sealed this 27th day of May 1975.

(SEAL)
Attest:

RUTH C. MASON
Attesting Officer

C. MARSHALL DANN
Commissioner of Patents
and Trademarks